United States Patent [19]

Hardy

[11] Patent Number: 5,398,684

[45] Date of Patent: * Mar. 21, 1995

[54] METHOD AND APPARATUS FOR VIDEO PRESENTATION FROM SCANNER IMAGING SOURCES

[76] Inventor: Tyrone L. Hardy, 13433 Caminito Carmel, Del Mar, Calif. 92014

[*] Notice: The portion of the term of this patent subsequent to Mar. 31, 2009 has been disclaimed.

[21] Appl. No.: 860,926

[22] Filed: Mar. 31, 1992

Related U.S. Application Data

[63] Continuation of Ser. No. 290,316, Dec. 23, 1988, Pat. No. 5,099,846.

[51] Int. Cl.$^6$ .............................................. A61B 5/05
[52] U.S. Cl. ............................ 128/653.1; 128/653.2; 606/130; 364/413.13; 364/413.14; 364/413.22
[58] Field of Search ........................ 128/653.1, 653.2; 606/130; 364/413.13, 413.15, 413.19, 413.22

[56] References Cited

U.S. PATENT DOCUMENTS

| | | | |
|---|---|---|---|
| 3,508,552 | 4/1970 | Hainault | 128/303 |
| 3,783,251 | 1/1974 | Pavkovich | 235/151 |
| 3,987,281 | 10/1975 | Hodes | 235/151.3 |
| 4,079,450 | 3/1978 | Grimm et al. | 364/200 |
| 4,123,143 | 10/1978 | Yachim et al. | 350/171 |
| 4,223,227 | 9/1980 | Horwitz | 250/491 |
| 4,230,117 | 10/1990 | Anichkov | 128/303 B |
| 4,259,725 | 3/1981 | Andrews et al. | 364/521 |
| 4,278,888 | 7/1981 | Wagner | 250/445 T |
| 4,341,220 | 7/1982 | Perry | 128/630 |
| 4,350,159 | 9/1982 | Gouda | 128/303 B |
| 4,386,602 | 6/1983 | Sheldon et al. | 128/4 |
| 4,455,609 | 6/1984 | Inamura et al. | 364/414 |
| 4,463,758 | 8/1984 | Patil et al. | 128/303 B |

(List continued on next page.)

FOREIGN PATENT DOCUMENTS 2384481 11/1978 France .
1074239 4/1982 U.S.S.R. .

OTHER PUBLICATIONS

"Computerized Optimization of $^{125}$I Implants in Brain Tumors" by B. Bauer-Kirpes, Ph.D. *J. Radiation Oncology Biol. Phys.*, vol. 14, pp. 1013-1023 (1987).

"External Stereotactic Irradiation by Linear Accelerator" by F. Columbo, M.D., et al. *Neurosurgery*, vol. 16, No. 2; pp. 154-159 (1985).

Advertisement: "Elekta" Leksell Micro-Stereotactic System (1989).

"The University of Florida Radiosurgery System" by W. A. Friedman, M.D. 1989, Elsevier Science Publishing Company, Inc.

"Stereotactic CT Atlases" by Tyrone L. Hardy *Modern Stereotactic Surgery*, L. D. Lunsford, Ed., Boston, Mass.; pp. 425-439 (1988).

"CASS: A Program for Computer-Assisted Stereotaxic Surgery", *Proceedings of the 5th Annual Symposium on Computer Application in Medical Care*, T. L. Hardy and J. Koch; Washington, D.C., 1981, pp. 1116-1126.

(List continued on next page.)

*Primary Examiner*—Ruth S. Smith
*Attorney, Agent, or Firm*—Deborah A. Peacock; Jeffrey D. Myers; Donovan F. Duggan

[57] ABSTRACT

The disclosure is directed to a method and apparatus for presenting a plurality of scanning images in a video presentation. The disclosure is particularly directed to the use of such an apparatus and method in stereotactic surgery, wherein acquisition of a plurality of scanner images, conversion of these images into a selected standard format, storage of the acquired and converted images, selective recall and display of at least two of the images, and independent manipulation of each of the images for comparison are provided. Probe placement can be simulated and the images can be enhanced in various ways. The images used can be, for example, CT, PET, X-ray, DSA, isotope, and NMR scans. Brain map atlas images can be superimposed on and fitted to the scan images of a particular brain. Video displays of three dimensional simulations can also be produced.

109 Claims, 8 Drawing Sheets

Microfiche Appendix Included
(8 Microfiche, 74 Pages)

U.S. PATENT DOCUMENTS

| | | | |
|---|---|---|---|
| 4,502,147 | 2/1985 | Michaels | 378/206 |
| 4,583,538 | 4/1986 | Onik et al. | 128/303 |
| 4,597,380 | 7/1986 | Raif et al. | 128/6 |
| 4,598,368 | 7/1986 | Umemura | 364/413.22 |
| 4,608,635 | 8/1986 | Osterholm | 364/414 |
| 4,608,977 | 9/1986 | Brown | 128/303 B |
| 4,617,925 | 10/1986 | Laitinen | 128/303 B |
| 4,618,978 | 10/1986 | Cosman | 378/164 |
| 4,638,798 | 1/1987 | Shelden et al. | 128/303 B |
| 4,651,732 | 3/1987 | Frederick | 128/303 R |
| 4,653,112 | 3/1987 | Ouimette | 382/69 |
| 4,702,571 | 10/1987 | Barber | 350/516 |
| 4,706,665 | 11/1987 | Gouda | |
| 4,719,585 | 1/1988 | Cline et al. | 364/518 |
| 4,729,098 | 3/1988 | Cline et al. | 364/414 |
| 4,729,099 | 3/1988 | Iverson et al. | 364/414 |
| 4,770,182 | 9/1988 | Damadian et al. | 128/653.2 |
| 4,777,598 | 10/1988 | Kellar et al. | 364/413.22 |
| 4,790,026 | 12/1988 | Gennery et al. | 382/49 |
| 4,791,934 | 12/1988 | Brunnett | 128/653.1 |
| 4,813,588 | 3/1989 | Srivastava et al. | 228/103 |
| 4,832,049 | 5/1989 | Matsushita et al. | 128/781 |
| 4,835,712 | 5/1989 | Drebin et al. | 364/518 |
| 4,856,528 | 8/1989 | Yang et al. | 128/653 |
| 4,884,566 | 12/1989 | Mountz et al. | 606/130 |
| 4,888,713 | 12/1989 | Falk | 364/522 |
| 4,905,702 | 3/1990 | Foss | 128/665 |
| 4,919,516 | 4/1990 | Petran et al. | 350/171 |
| 4,976,680 | 12/1990 | Hayman et al. | 600/7 |
| 4,977,505 | 12/1990 | Pelizzari et al. | 364/413.13 |
| 5,027,818 | 7/1991 | Bova et al. | 128/653 R |
| 5,094,241 | 3/1992 | Allen | 606/130 |
| 5,099,846 | 3/1992 | Hardy | 128/653.1 |

OTHER PUBLICATIONS

"Computer-Assisted Stereotactic Surgery," Hardy, T. L. and Koch, J.; *Appl. Neurophysiol.*, vol. 45, pp. 396–398 (1982).

"Computer Graphics with Computerized Tomography for Functional Neurosurgery," Hardy, T. L., Koch, J., and Lassiter, A., *Appl. Neurophysiol.*, vol. 46, pp. 217–226 (1983).

"A Portable Computerized Tomographic Method for Tumor Biopsy," Hardy, T. L., Lassiter, A., and Koch, J., *Acta. Neurochir.* [Suppl.], (Wien) p. 444 (1983).

"Computer-Assisted Stereotactic Laser Microsurgery for the Treatment of Intracranial Neoplasms" by P. Kelly et al. *Neurosurgery*, vol. 10, No. 3, pp. 324–331 (1982).

"Computer Simulation for the Stereotactic Placement of Interstitial Radionuclide Sources onto CT-Defined Tumor Volumes," Kelly et al., *Neurosurgery*, pp. 412–444 (1984).

"Stereotactic Surgical System Controlled by Computed Tomography" by M. Koslow, M.D., et al. *Neurosurgery*, vol. 8, pp. 72–82 (1981).

"The Ill-Conditioning in Stereotaxic Irradiation: Optimization of Isodoses Arrays Distribution Using the Singular Values Decomposition," Conference *Eighth International Conference*, Jun. 8–10, 1988.

"Exploring Design Space: Optimization as Synthesizer of Design and Analysis" by A. R. Parkinson et al. *Computers in Mechanical Engineering*, Mar. 1985, pp. 28–36.

"The Role of Computed Tomography and Digital Radiographic Techniques in Stereotactic Procedures for Electrode Implantation and Mapping, and Lesion Localization," by T. M. Peters et al., *Appl. Neurophsyiol.*, vol. 46, pp. 200–205 (1983).

"Measurements of Dose Distributions in Small Beams of 6MV X-Rays" by R. K. Rice et al. *Phys. Med. Biol.*, vol. 32, No. 9 (1987), pp. 1087–1099.

"Development of a Computerized Microstereotaxis Method for Localization and Removal of Minute CNS Lesions Under Direct 3-D Vision" by C. H. Shelden et al. *Journal of Neurosurgery*, Technical Report, vol. 52, pp. 21–27 (1980).

Sales Brochure of Stereotactic Medical Systems, Inc., designed by Patrick Kelly et al.

"A System for Anatomical and Functional Mapping of the Human Thalamus" by C. J. Thompson et al. *Computers and Biomedical Research* (1977), pp. 9–24.

"A CT-Based Computerized Treatment Planning System for I-125 Stereotactic Brain Implants" by K. Weaver, Ph.D., et al. *J. Radiation Oncology Biol. Phys.*, vol. 18, pp. 445–454 (1989).

"Linear Accelerator as a Neurosurgical Tool for Stereotactic Radiosurgery" by K. R. Winston, M.D., et al. *Neurosurgery*, vol. 22, No. 3 (1988), pp. 454–462.

"Anatomy of the Thalamus," G. Schaltenbrand and P. Bailey, eds., *Introduction to Stereotaxy with an Atlas of the Human Brain*, vol. 1; Stuttgart: Thieme, 1959, pp. 230–290—textbook.

"Variations and Connections of the Human Thalamus," Van Buren, J. M. and Borke, R. C. (Springer, New York (1972))—textbook.

*Atlas for Stereotaxy of the Human Brain*, G. Schaltenbrand and W. Wahren (2nd ed.), Stuttgart: Thieme, 1977—textbook.

"Preliminary Experience with Brown-Roberts-Wells (BRW) Computerized Tomography Stereotaxis guidance System," by M. Peter Heilbrun et al., J. Neurosurg., vol. 59, pp. 217–222 (Aug. 1983).

(List continued on next page.)

OTHER PUBLICATIONS

"A Computerized System for the Elastic Matching of Deformed Radiographic Images to Idealized Atlas Images" by R. Bajcsy et al., Journal of Computer Assisted Tomography, vol. 7, No. 4, pp. 618–625 (Aug. 1983).

"Computerized Optimization of Treatment Planning in the Brachytherapy of Brain Tumors" by B. Bauer et al., Proceedings of the Eighth International Conference on the Use of Computers in Radiation Therapy, IEEE Computer Society, pp. 395–398 (1984).

"Display of Organs and Isodoses as Shaded 3-D Objects for 3-D Therapy Planning" by B. Bauer-Kirpes et al., Int. Radiation Oncology Biol. Phys., vol. 13, No. 1, pp. 135–140 (Jan. 1987).

"Treatment Planning and Image Correlation for Dynamic Radiotherapy of Small Target Volumes in Brain" by R. Boesecke et al., European Society for Therapeutic Radiology and Oncology, 7th Annual Meeting, Program Abstract (Sep. 1988).

"Medical Workstation for Radiation Therapy Planning" by R. Boesecke et al., Proceedings of the Ninth International Conference on the Use of Computers in Radiation Therapy, *The Use of Computers in Radiation Therapy*, Ch. 46, pp. 181–183 (Jun. 1987).

"Structure Transfer Between Sets of Three Dimensional Medical Imaging Data" by G. T. Y. Chen et al., Proceedings of the Sixth Annual Conference and Exposition of the National Computer Graphics Association, vol. 3, pp. 171–177 (Apr. 1985).

"Use of a TV Digitizer for the Evaluation of Dosimetric Films" by J. Doll et al., Proceedings of the World Congress on Medical Physics and Biomedical Engineering (Sep. 1982).

"Stereotactic Localization of Small Subcortical Brain Tumors for Open Surgery" by M. I. Haris et al., Surg. Neurol., vol. 28, pp. 345–350 (1987).

"Comprehensive Computer-Assisted Data Collection Treatment Planning and Interactive Surgery" by B. A. Kall et al., SPIE, vol. 767, *Medical Imaging*, pp. 509–514 (1987).

"Methodology and Clinical Experience with Computed Tomography and a Computer-resident Stereotactic Atlas" by B. A. Kall et al., Neurosurgery, vol. 17, No. 3, pp. 400–407 (1985).

"Computer Assisted Stereotactic Biopsies Utilizing CT and Digitized Arteriographic Data" by P. J. Kelly et al., Acta Neurochirurgica, Suppl. 33, pp. 233–235 (1984).

"Stereotactic CT Scanning for the Biopsy of Intracranial Lesions and Functional Neurosurgery" by P. J. Kelly et al., Appl. Neurophysiol., vol. 46, pp. 193–199 (1983).

"Functional Stereotactic Surgery Utilizing CT Data and Computer Generated Stereotactic Atlas" by P. J. Kelly et al., Acta Neurochirurgica, Suppl. 33, pp. 577–583 (1984).

"Method of Computed Tomography-based Stereotactic Biopsy with Arteriographic Control" by P. J. Kelly et al., Neurosurgery, vol. 14, No. 2, pp. 172–177 (1984).

"CT-Guided Ablative Stereotaxis Without Ventriculography" by L. V. Laitenen, Appl. Neurophysiol., vol. 48, pp. 18–21 (1985).

"Noninvasive Multipurpose Stereoadapter" by L. V. Laitenen, Neurological Research, vol. 9, pp. 137–141 (Jun. 1987).

"An Interstitial Implant Technique Evaluated by Contiguous Volume Analysis" by D. L. Neblett et al., Endocurie, Hypertherm, Oncol., vol. 1, pp. 213–221 (Oct. 1985).

"Three Dimensional Image Correlation of CT, MR, and PET Studies in Radiotherapy Treatment Planning of Brain Tumors" by L. R. Schad et al., Journal of Computer Assisted Tomography, vol. 11, No. 6, pp. 948–954 (Nov. 1987).

"Stereotactic Percutaneous Single Dose Irradiation of Brain Metastases with a Linear Accelerator" by V. Sturm et al., Int. J. Radiation Oncology Biol. Phys., vol. 13, No. 2, pp. 279–282 (Feb. 1987).

"Stereotactic Computer Tomography with a Modified Riechert–Mundinger Device as the Basis for Integrated Stereotactic Neuroradiological Investigations" by V. Sturm et al., Acta Neurochirurgica, vol. 68, pp. 11–17 (1983).

"Digital Image Review Console" by R. Vercillo et al., SPIE, vol. 767, *Medical Imaging*, pp. 708–712, (Feb. 1987).

METHOD AND APPARATUS FOR VIDEO PRESENTATION FROM SCANNER IMAGING SOURCES

This is a continuation of application Ser. No. 07/290,316, filed on Dec. 23, 1988, now U.S. Pat. No. 5,099,846.

A portion of the disclosure of this patent document contains material which is subject to copyright protection. The owner has no objection to the facsimile reproduction by anyone of the patent document or the patent disclosure, as it appears in the Patent and Trademark Office patent file or records, but otherwise reserves all copyright rights whatsoever.

Computer program listings comprising sequences of instructions, routines, and other contents are provided in the microfiche appendix, which is incorporated herein by reference. The microfiche appendix consists of 8 sheets of microfiche, each sheet having 65 frames, not all of which have been used.

1. FIELD OF THE INVENTION

The invention relates to video presentation and more particularly to a method and apparatus for generating a video presentation from a variety of scanner imaging sources, in particular for stereotactic surgery.

2. BACKGROUND OF THE INVENTION

Stereotactic surgical techniques allow physiological exploration and/or destruction of deep cerebral or spinal cord structures which are invisible from the surface, but which location can be determined by a knowledge of their coordinates in space relative to known anatomical and topographical landmarks. The use of stereotaxis in neurosurgical techniques seeks to avoid open operative approaches to these areas with a minimum of disturbance to surrounding structures. The technique generally involves the placement of fine electrodes or probes in strategic "target areas" which may comprise specific functional anatomical sites or morphological lesions or abnormalities. One of the major difficulties of stereotactic surgery is graphic conceptualization of the location of surgical probes inserted into deep brain structures. Not only is the probe out of the surgeon's sight, but it is tilted, rotated, and extended in many different directions, which circumstance makes it almost impossible for the surgeon to maintain a mental picture of the location of the probe in the brain core. The surgeon must imagine the location of the probe while taking into account the forward and lateral angles of the probe, the distance of the probe from the target, the direction that the electrode extends from the probe, and many other angular variables. Furthermore, the coordinate system of the stereotactic frame seldom corresponds to the "brain coordinate system," causing greater margin of error and difficulty in placement of the probe. Stereotactic surgery, therefore, is essentially a "blind" surgical procedure with many complex geometric variables. Any system which will enhance the surgeon's conceptualization of the procedure will greatly enhance its efficacy.

The introduction of stereotaxis to the armamentarium of human neurosurgical technique has been an important addition. This is evident by its use in the treatment of many neurological disorders. This technique has expanded from its earlier use, primarily in the treatment of dyskinesias and pain syndromes, to include the treatment of seizure disorders, aneurysms, brain tumors and many other neuropathological conditions. In recent years there has been a significant increase in the number and use of stereotactic surgical techniques. This has been brought about by the development of new imaging technologies, for example, computerized axial tomography (CT), nuclear magnetic resonance (NMR) scanning, various radioisotope scanning techniques, and digital subtraction angiography (DSA). These imaging techniques allow the surgeon to "see" certain brain structures and to use these imaging technologies to aid in planning stereotactic surgical procedures.

Computed tomography (CT) is well established as a valuable diagnostic and investigative imaging device and has revolutionized the evaluation and treatment of neurological conditions. Applications and use of CT technology with stereotactic and functional neurosurgery are increasing. Advancing computer technology has been the basis upon which CT scanning technology has developed; this same technology is supporting the development of the newer digital subtraction angiographic (DSA), various radioisotope scanning, and nuclear magnetic resonance (NMR) imaging systems.

The increased resolution afforded by such scanning systems allows direct identification of brain structures that could only be inferred from conventional roentgenological techniques. Stereotactic surgery, being primarily a procedure performed without the aid of direct visualization, is dependent on sophisticated imaging techniques for its accurate execution. Therefore, it necessarily follows that as computer and imaging technology improve, so do the possibilities of stereotactic surgery. The present invention is primarily concerned with the use of computer-graphics techniques and scanning techniques for generating various composite images to better aid the stereotactic surgeon in localizing structures, such as subcortical structures, lesions, or abnormalities.

Non-computer systems have been developed in the art for stereotactic surgery. These systems use spatial coordinate determinations based upon the use of special plastic type grids and measurement devices. These systems are based upon hand plotting and calculation of coordinate positions. Some disadvantages to such systems are that they are cumbersome, slow, relatively inaccurate, have very limited use, and are specific for only one type of scanning device and manufacturer.

Software routines on hand-held calculators, e.g., HP41C, Sharp, and Epson HX20, have also been developed in the art for use with stereotactic surgery. Calculations are done by the use of a calculator instead of a grid and specific measuring instruments. Parameters for coordinate determination are entered into the calculator's functions by the use of similar grids. Some disadvantages of these systems are the same as the non-computer spatial coordinate systems described above.

Some parent scanning devices, e.g., CT scanner, NMR scanner, etc., contain resident software systems. Rule grids are placed over the image in the scanner via a software graphics package of limited capabilities. Accuracy is limited, since measurements are done in "screen coordinates" and therefore the systems do not take into consideration various rotations of the patient's head or other body parts in the scanning device. These are purely systems for calculating coordinates and have no operative simulating capabilities. CT scanners and NMR scanners also have some image manipulation routines which consist of various means of ramping image grey scales for contrasting; however, they contain none of the other features of the present invention, such as brain anatomical mapping techniques, electrophysiological mapping, extensive image manipulation, image comparison, 3-D simulations, etc. By design, each of these systems is limited to use in a specific scanner and its use must be sanctioned by the scanner designer, such as shown in "The Role of Computed Tomographic and Digital Radiographic Techniques in Stereotactic Procedures for Electrode Implantation and Mapping, and Lesion Localization," by T. M. Peters, et al., *Appl. Neurophysiol.*, Vol. 46, pp. 200–205 (1983). Image sources from several different scanners cannot be compared. Too, all functions must be carried out in each specific scanner device which monopolizes the scanner's use. Another disadvantage is that improvements or modifications to these systems cannot be made as scanner manufacturers tend to resist or disallow the addition of non-proprietary software and/or hardware to their scanning systems since they are potentially at risk of incurring additional liability should the software and/or hardware not function as intended.

Other prior art systems utilize IBM PC type computers, including clones, and other desktop type personal computer versions. In some of these versions, either a camera input interface is used to acquire scan images from an X-ray plate type hard copy into the computer's video display, or magnetic transport media is utilized, most notably magnetic computer tapes. One disadvantage of these systems is that these existing interface designs rely upon the digitized images acquired through a camera input. The camera is mounted over an X-ray type hard copy image of the scanner image section to obtain an image. These systems can be inherently inaccurate because they use various kinds of camera lens designs and different image aberrations result from different lens designs. These include warping and distortion of the image due to chromatic aberration, spherical aberration, coma, astigmatism, and various other aberrations which result from deviation of refracted or reflected light rays from a single focus, or their convergence to different foci, due to the spherical shape of the lens or mirror. It is difficult to adjust or compensate for these problems. Another disadvantage is that existing interface designs rely upon the transportation of digital data from the original scanning source via use of magnetic transport media, most commonly tapes or floppy disks. Such transport media are not standardized and different scanner manufacturers use different digital formatting methods and formats in their systems. Marketing and servicing any system utilizing magnetic transport media to obtain images is extremely difficult due to tremendous and variable software overhead and frequently incompatible hardware designs of magnetic tape and disk drives. Such systems are heavily dependent upon acquiring proprietary information from the scanning device manufacturers with regards to how their image is digitally formatted. The digital format of images varies considerably among scanner types, scanner manufacturers, and even scanner versions from a single manufacturer. Transportation and use of such systems has to be custom designed for each scanner at different institutions and frequently has to be changed, depending upon the particular image formatting version used at an institutional scanning site. Software overhead is therefore extensive and almost impossible to service. Furthermore, these systems are difficult to use since there is also considerable incompatibility among tape manufacturers, tape reading methods, and hardware. Such systems can be quite confusing for the user. Furthermore, such systems have limited use since they do not have the computer processing power which is currently available in faster outputting systems, and have no specific means of comparing images from different scanning sources. Some of these systems, however, have some rudimentary image manipulation and simulation capabilities.

Devices utilizing large computer systems which use magnetic transport media and multiple image displays also exist. There is currently one system apparently available for use which is resident in a large scanner computer which uses a tape interface for acquiring images from several sources and displays the images on a plurality of monitors. One disadvantage of such device, as previously discussed, concerns the inherent difficulties associated with magnetic transport media. In addition, difficulties encountered with resident software systems, also previously discussed, are present in this large computer using system. This system is additionally particularly large and costly and requires a computer engineer to competently operate the system, which is beyond the ability of the average neurosurgeon to operate by himself. Significantly, separate images from separate sources cannot be compared one to another or overlayed in the system. And, because of the system's very large size, it has to be housed in a separate operative suite which adds to its expense. A prior device designed by Patrick Kelly, et al., manufactured by Stereotactic Medical Systems, Inc., is such a system as described above.

The images acquired by these various prior art scanning techniques are not standardized in a common format and no method for comparing and using images from various scanners has been developed. The method and apparatus of the present invention have solved this problem, as well as other problems discussed above.

Another prior art imaging system, developed by Tyrone L. Hardy, M.D., and others (Thompson, C. J., Hardy, T. L., and Bertrand, G.; "A System for Anatomical and Functional Mapping of the Human Thalamus," *Comput Biomed Res.*, Vol. 19, pp 9–24, 1977) was designed to run on a Digital Equipment Corporation PDP-12 computer with software written in assembly-level and Fortran IV languages. This system was very large and could not be taken into an operating room. The graphics display terminal, which could be taken separately into the operating room, had to be interfaced with the computer by long coaxial linkages. Its operation was cumbersome but necessary, given the hardware constraints inherent in the computer design. Stereotactic brain maps of the diencephalon were utilized in this system. These stereotactic brain maps were the architectonics by R. Hassler ("Anatomy of the Thalamus;" *Introduction to Stereotaxy with an Atlas of the Human Brain,* Vol 1; G. Schaltenbrand and P. Bailey, eds. Stuttgart: Thieme, 1959, pp. 230–290) and Van Buren and Borke (Van Buren, J. M., and Borke, R. C.: "Variations and Connections of the Human Thalamus" (Springer, New York, 1972)), which were digitized for use in the computer. Software routines for modifying the computer displays of the brain maps corrected deficiencies in anatomical sectioning (the horizontal sections vary 8 degrees from the intercommissural plane) and variations in the sizes of the atlas maps (the frontal maps were considerably smaller than the horizontal maps). The coordinate system for the digitized atlas map sections were based, as those of the anatomical atlas maps, on a brain coordinate system constructed about the third ventricular core; that is, an intercommissural line bisected by a midcommissural line and a horizontal line representing the basal plane of the brain. This system was later extensively modified to operate in a much smaller portable computer system by Tyrone L. Hardy and Jay Koch (T. L. Hardy and J. Koch, "CASS: A Program for Computer Assisted Stereotaxic Surgery," *Proceedings of the 5th Annual Symposium on Computer Application in Medical Care;* Washington, D.C., 1981, pp. 1116–1126), which describes a system which ran on a smaller, more portable DEC PDP-11 MINC computer system with a Tektronix graphics terminal. This system was designed to work with older X-ray imaging technology and not with CT scans, NMR scans or PET or DSA. The system drew map images, simulated probe trajectories and printed electrophysiological data on the display terminal according to various parameters which were typed into certain program requests.

Brain stem and cerebellar maps from the newer Schaltenbrand and Wahren atlas (G. Shaltenbrand and W. Wahren, *Atlas for Stereotaxy of the Human Brain* (2d Ed.); Stuttgart: Thieme, 1977) afforded an opportunity to expand the computer mapping capabilities to include rhombencephalic structures. Incorporating these maps into this system required the development of a coordinate system that would allow the simultaneous display of diencephalic architectonics and the remaining brain stem and cerebellum. Allowance was also required for variations in the angle of the junction of the diencephalon with the lower brain stem. See Hardy, T. L., Koch, J., "Computer-assisted Stereotactic Surgery," *Appl. Neurophysiol* . Vol. 45, pp. 396–398, 1982, which describes a software modification to the above-noted system described in the 1981 paper to allow a similar use of brain stem maps and describes the development of a brain stem coordinate system. Both coordinate systems could be moved independently of each other; the size of the brain maps, including the brain-stem length, could be readily varied to match the patient's anatomical dimensions as determined from contrast ventriculograms. This was accomplished by developing a method of intersecting an upper (diencephalic) coordinate system constructed about the third ventricular core, with a lower coordinate system constructed about the fourth ventricle. For example, the angle of intersection will be closer to 90 degrees in a patient with a brachiocephalic brain in which brain-stem angulation is perpendicularly oriented. Adjustments for difference in brain-stem sizes were achieved by a software subroutine that could be prompted to expand or contract the digitized maps. As with the above-noted system described in the 1981 paper, this system was not designed to work with newer imaging technology. After the development of high-resolution, color-graphics raster display monitors that could interface with small computer systems it became possible to improve this system. The computer system was later modified so that it could use such a monitor to display CT images as well as benefit from the addition of color graphics. The result was a portable system which could store, manipulate, and selectively display CT images in the operating room independent of the CT scanner. The previously digitized atlas maps also could be superimposed on CT sections of the diencephalon. This method of graphic operative simulation served as a guide for using CT data in performing functional neurosurgery. However, this system had to be programmed separately for each type of scanner. "Computer Graphics with Computerized Tomography for Functional Neurosurgery, (T. L. Hardy, J. Koch, and A. Lassiter, *Appl. Neurophysiol.* Vol. 46, pp. 217–226 (1983)), describes a prototype system which could be used with CT imaging technology. This system could simulate probe trajectories but could not determine coordinates. Such parameters had to be entered by typed entry into the computer's program. The system was capable of pseudocolor, but no other image manipulation routines were possible. CT image display was limited to four bits of image capabilities which gave a gray scale capability of $2^4$ (16 levels). This system was fraught with difficulties and the hardware design was subsequently abandoned. Some of these difficulties were also due to the CPM based operating system which was slow, cumbersome and extremely difficult to use as a developmental platform. Hardy, T. L., Lassiter, A., and Koch, J., "A Portable Computerized Tomographic Method for Tumor Biopsy", *Acta. Neurochir.* [Suppl.], (Wien), p. 444, 1983, describes the above-noted system as a laboratory model for simulating tumor biopsy.

SUMMARY OF THE INVENTION

In accordance with the present invention, there is provided a method and apparatus for generating a video presentation of images from a variety of separate scanner imaging sources. The method of the invention comprises the steps of acquiring a plurality of images from a variety of separate scanner imaging sources, converting the acquired images into a selected format, storing the acquired and converted plurality of images, selectively recalling and displaying at least two of the stored plurality of images, and independently manipulating each of the selected images and comparing the selected images. The manipulating step preferably comprises shaping and sizing at least one of the selected images to conform to at least one other selected image in shape and size. The method may further comprise superimposing at least one selected image upon at least one other selected image. The method may also comprise a step of comparing the selected images, contrasting characteristics of at least two selected images using at least one of the procedures of filtering, smoothing, sharpening, pseudo-coloring and edge detection. The edge detection procedure can be, for example, a Laplacian, a Roberts, a Sorbel, or a Frei procedure. The image acquiring step can comprise obtaining at least one image directly from a scanner without the use of magnetic transport media. The sequence of steps taken by a user can be recorded and archived.

The method of the invention is preferably practiced in stereotactic surgery, and comprises generating a video presentation of brain images from a variety of separate brain scanner imaging sources to provide a representation of the anatomical and physiological configuration of the brain of a patient. The method comprises the steps of acquiring a plurality of brain-related images from a variety of separate brain scanner imaging sources, at least one such image being of the actual patient's brain, converting the acquired images into a selected format, storing the acquired and converted plurality of images, selectively recalling and displaying at least two of the stored plurality of images, and independently manipulating at least one of the selected images and comparing the manipulated image to at least one other of the selected images. The acquiring step can comprise obtaining images from a brain map atlas and the manipulation step comprises fitting at least one map from the atlas to at least one selected image of the patient's brain. The manipulating step can comprise shaping and sizing at least one of the selected images to conform to at least one other selected image in shape and size. The method can further comprise superimposing at least one selected image upon at least one other selected image. The step of comparing the selected images can comprise contrasting characteristics of at least two selected images using filtering, smoothing, sharpening, pseudocoloring, or edge detection. The edge detection procedure can be a Laplacian, Roberts, Sorbel, or Frei procedure. The method can additionally comprise the step of measuring the distance between two points within the actual patient's brain, the area of a selected portion of the brain, and the volume of a selected part of the brain. The method can comprise generating a simulated three-dimensional image of the actual patient's brain, the three-dimensional simulation image preferably being representative of an image such as a computerized axial tomography (CT) image, a nuclear magnetic resonance (NMR) image, a positron emission tomography (PET) image, a digital subtraction angiography (DSA) image, isotope image, and an X-ray image. The three-dimensional simulation image comprises a composite of images from more than one source. The method can further comprise a step for determining optimum placement or dosage for an isodose implantation. An archiving step can be used to record and store the steps taken by a user.

The invention additionally comprises an apparatus for generating a video presentation of images from a variety of separate scanner imaging sources. The apparatus comprises structure for acquiring a plurality of images from a variety of separate scanner imaging sources and for converting the acquired images into a selected format. Storage is provided for the acquired and converted plurality of images. Structure for selectively recalling and displaying at least two of the stored plurality of images, for independently manipulating each of the selected images and for comparing the selected images is also provided. The image manipulating structure preferably comprises structure for shaping and sizing at least one of the selected images to conform to at least one other selected image in shape and size. The apparatus can further comprise structure for superimposing at least one selected image upon at least one other selected image. The structure for comparing the selected images preferably comprises structure for contrasting characteristics of at least two selected images using filtering, smoothing, sharpening, pseudocoloring, or edge detection. The edge detection procedure can be a Laplacian, a Roberts, a Sorbel, or a Frei procedure. The image acquiring structure can comprise structure for obtaining at least one image directly from a scanner without the use of magnetic transport media. Storage or archiving means can be provided for storing the user's procedural steps.

The apparatus of the invention is preferably for use in stereotactic surgery and comprises an apparatus for generating a video presentation of brain images from a variety of separate brain scanner imaging sources to provide a representation of the anatomical and physiological configuration of the brain of a patient. The apparatus comprises structure for acquiring a plurality of brain-related images from a variety of separate brain scanner imaging sources, at least one such image being of the actual patient's brain, structure for converting the acquired images into a selected format, structure for storing the acquired and converted plurality of images, for selectively recalling and displaying at least two of the stored plurality of images, for independently manipulating at least one of the selected images and for comparing the manipulated image to at least one other of the selected images. The image acquiring structure preferably comprises structure for obtaining images from a brain map atlas and the image manipulation structure preferably comprises structure for fitting at least one map from the atlas to at least one selected image of the patient's brain. The manipulating structure preferably comprises structure for shaping and sizing at least one of the selected images to conform to at least one other selected image in shape and size. The apparatus can further comprise structure for superimposing at least one selected image upon at least one other selected image. The structure for comparing the selected images can comprise structure for contrasting characteristics of at least two selected images using filtering, smoothing, sharpening, pseudocoloring, or edge detection. The edge detection procedure can be a Laplacian, a Roberts, a Sorbel, or a Frei procedure. The apparatus can further comprise structure for simulating a brain probe and structure for simulating manipulation of the probe within a video presentation. The apparatus can further comprise structure for simulating one or more electrodes and for simulating manipulation of electrodes within a video presentation. The apparatus can further comprise structure for storing representations of physiological response points and for selectively recalling and displaying any of the response points within a video presentation. The apparatus can further comprise structure for providing stereotactic coordinates for a user selected point on a video presentation. The image acquiring structure preferably comprises structure for acquiring an image from a CT scanner, an NMR scanner, a PET scanner, an X-ray scanner, a DSA scanner and/or an isotope scanner. The image acquisition structure is preferably uniquely programmable to acquire any of a predetermined number of image types. The apparatus preferably further comprises structure providing for user to input within a sterile environment, such as an infrared grid disposed across the image displaying screen. The apparatus preferably further comprises structure for measuring distances, volumes and areas within an actual patient's brain. The apparatus further preferably comprises structure for generating a simulated three-dimensional image of the actual-patient's brain, the simulated three-dimensional image preferably being representative of a CT image, an NMR image, a PET image, a DSA image, isotope or an X-ray image. The image can comprise a composite of images from more than one source. The apparatus can further comprise simulated three-dimensional images comprised of a composite of images from more than one source. The apparatus can further comprise structure for determining optimum placement or dosage for an isodose implantation. A recording or archiving device for storing user procedure can be provided.

One object of the present invention is to provide a user with a video presentation of an image from one of a variety of imaging sources.

Another object of the present invention is to convert images from a variety of incompatible sources into a common format for storage, display and comparison.

Yet another object of the present invention is to provide a user with the capability of sizing and shaping one or more stored images to conform to a selected image.

Still another object of the present invention is to provide simulated three-dimensional views of an object, such as a human brain, from a variety of stored images.

One advantage of the present invention is that a surgeon, particularly a neurosurgeon, can readily and accurately determine optimum probe implantation trajectories.

Another advantage of the present invention is that a variety of images from different sources can be readily compared.

Yet another advantage of the present invention is that images can be enhanced in many ways while being viewed by a user to provide a number of desired effects to maximize the value of such images to the user.

Still another advantage of the invention is that an apparatus in accordance therewith can be utilized within a sterile environment by medical personnel to review images from a variety of sources during a procedure.

Yet still another advantage of the invention is that in accordance therewith, a record can be made of the images reviewed, the length of time they were each reviewed and how each was enhanced, manipulated and otherwise used.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate a preferred embodiment of the present invention and, together with the description, serve to explain the principles of the invention. In the drawings.

DETAILED DISCUSSION OF A PREFERRED EMBODIMENT OF THE INVENTION

The computer assisted stereotactic surgery apparatus and method of the present invention comprise hardware components and associated software, providing to a stereotactic surgeon the ability to acquire digital images from many different scanner imaging sources, to store these images in a computer system independent of the original scanning device, and to display and manipulate the stored images, as desired. The invention is useful for performing functional and morphological stereotactical procedures, including but not limited to tumor biopsies, thalamotomies, such as for the treatment of dyskinesias, pain syndromes, seizure disorders, blood vessel abnormalities, and the diagnosis and treatment of a variety of other structural or functional abnormalities.

In the preferred embodiment, the images are obtained and converted to a common standard format, such as an RS-170 format, for comparison, independent manipulation and display with other graphics capability at any selected time, such as during a stereotactic operative procedure. The surgeon, therefore, has in one system, means of acquiring, comparing and manipulating images from many scanning sources, and can utilize this data to plan and perform stereotactic surgical procedures in a cost effective manner. A surgeon is able to interface directly with the system in a sterile fashion during an operative procedure. This latter capability is afforded in the preferred embodiment preferably by an infrared beam touch screen interface through software icons for system manipulation. In practicing the invention, the surgeon can use the various images and data independent of the original scanning devices.

The preferred embodiment of the invention can be used by a surgeon with a limited or rudimentary understanding of computer systems. Indeed, it is not required that a surgeon have any knowledge of computer systems in order to operate the preferred embodiment. This frees a surgeon of this additional and extensive responsibility.

Figure 1:
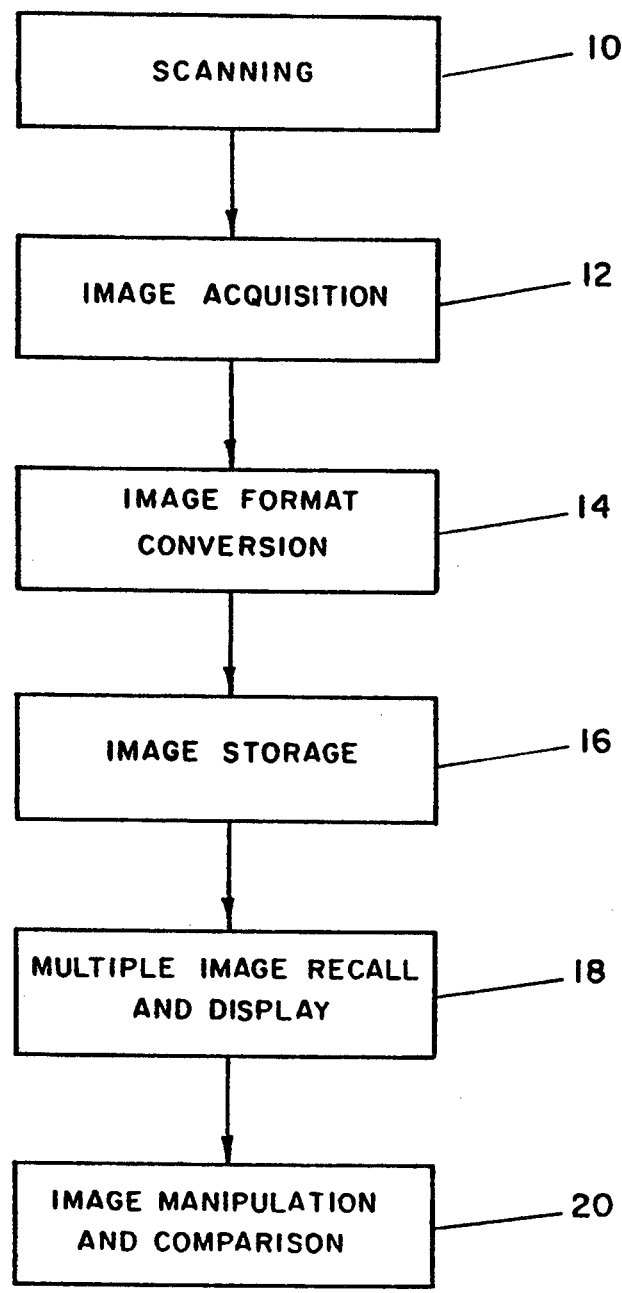
FIG. 1 schematically illustrates a preferred method of the invention.

The method of the invention is illustrated in FIG. 1. The method of the invention comprises scanning 10 the patient's head or other body part(s); image acquisition 12 of the scans obtained; image format conversion 14 for all images so that they are converted into the same format; image storage 16; multiple image recall and display 18 of the images; and image manipulation and comparison 20.

The preferred steps for practicing the method of the present invention are as follows:

a) Provide the apparatus in accordance with the invention in a scanner suite and connect the apparatus to a desired scanner, such as a CT, NMR, DSA, or isotope output scanner;

b) mount a stereotactic frame on the patient;

c) place the patient's head or other body part(s) to be analyzed in the scanner;

d) acquire the images desired using the scanner;

e) save or store the acquired images in the apparatus;

f) take the apparatus and the patient into the operating suite;

g) use the image manipulation routines in the apparatus to calibrate and preferably further enhance the desired image areas;

h) use any of the apparatus brain maps (preferably 117 brain maps) and the electrophysiological map system of the invention to precisely define the target area in functional stereotactic surgery or the volumetric and two- or three-dimensional simulation for morphological procedures;

i) use the apparatus to determine desired coordinates, such as the entry point, target point, or placement and trajectory of a probe for use in either functional stereotactic or morphological procedures; and j) prepare a tape archive of the entire operative procedure, if storage of data is desired.

Figure 2:
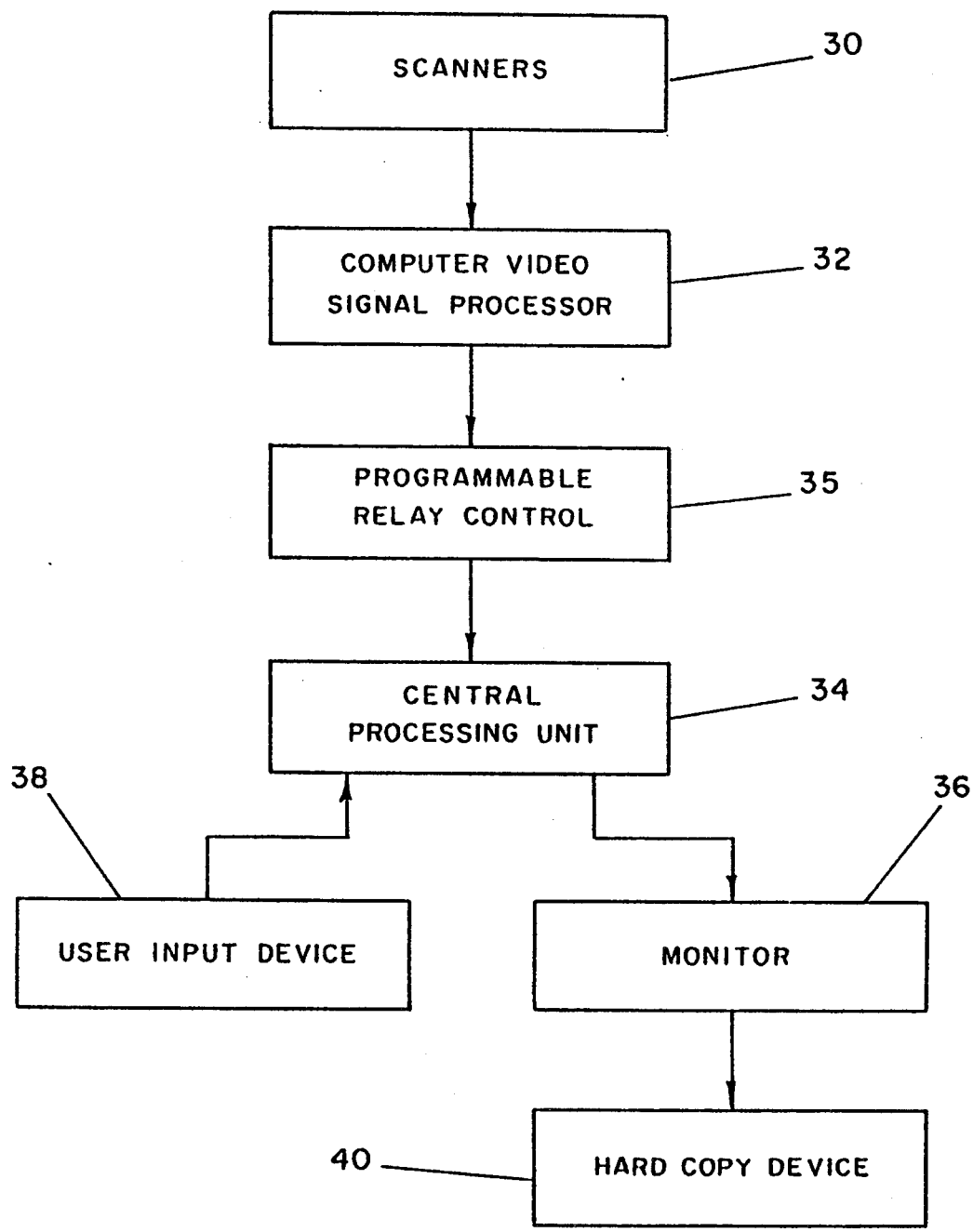
FIG. 2 illustrates a preferred hardware block diagram in accordance with the invention.

FIG. 2 illustrates a preferred hardware block diagram in accordance with the invention. Scanners 30, such as CT, magnetic resonance imaging (MRI), PET, DSA, X-ray and various isotope scanners, are provided to obtain various scanning data. This scanning data, which is in various, typically non-standard formats, is convertible to a standard format in accordance with the invention using a PROM computer video signal processor 32. Standard formats which can be used include, but are not limited to, RS-170, CCIR 625 I, RS-343, RS-422, and NTSC. The scanning data may be provided to the computer video signal processor 32 from the scanners 30 by, for example, a BNC connector. The converted scanning data is made available, through programmable relay control 35, to a central processing unit (CPU) 34, such as a 68020/030 VME BUS based CPU with a clock speed up to 30 MHz, preferably comprising hard disc storage, floppy disc storage, streamer tape storage, and a high-resolution frame grabber with a high speed graphics and video image processor. The programmable relay control 35 sets the scanner converter input/output parameters to acquire and convert scanner image data from its various formats to a standard format, for use by the system in accordance with the invention. Alternatively, a scanner converter automatically senses signal input and sets parameters for conversion to a standard format, without the use of user selectable switches. A user input device 38, such as a high-resolution infrared touch screen and a monitor 36, both connected to the CPU 34, enable the user to selectively manipulate and display the image data. The monitor 36 is preferably a high-resolution color graphics monitor with video inputs for red, green, blue, and composite video signals. The monitor 36 can be configured to operate in either interlaced or non-interlaced mode. Copies of images on the monitor can be provided using a hard copy device 40, such as a high resolution color videocopy unit.

Software, provided in the CPU 34, is preferably structured on a multi-modular bi-divisional foundation, which comprises a division for image acquisition, enhancement and manipulation and a division for graphics and user specific functions. The division for image acquisition, enhancement and manipulation includes modular software subroutines for: 1) image capture, storage, and archiving; 2) pixel analysis for an entire image or user-defined areas of interest; 3) zoom and pan functions; 4) contrasting and filtering images with functions for smoothing, sharpening, and pseudocoloring; 5) image comparisons; 6) image editing; and 7) various edge detection routines, including Laplacian, Roberts, Sorbel, and Frei routines. The graphics and user-specific functions comprise software modular subroutines that control: 1) the manipulation and swapping of diencephalic and brain-stem atlas maps (preferably at least 117 of such maps) in frontal, sagittal, and horizontal sections; 2) the graphic simulation and the manipulation of various probes and electrodes; 3) alphanumeric functions for demographic data and for coding, Storing, and selectively displaying the position of various electrophysiological response points on an electrophysiological map system which preferably comprises at least 2500 electrophysiological response points; 4) measurement functions for determining stereotactic coordinates and other user-specific calculations; and 5) volumetric determinations and two- or three-dimensional simulations.

Figure 3:
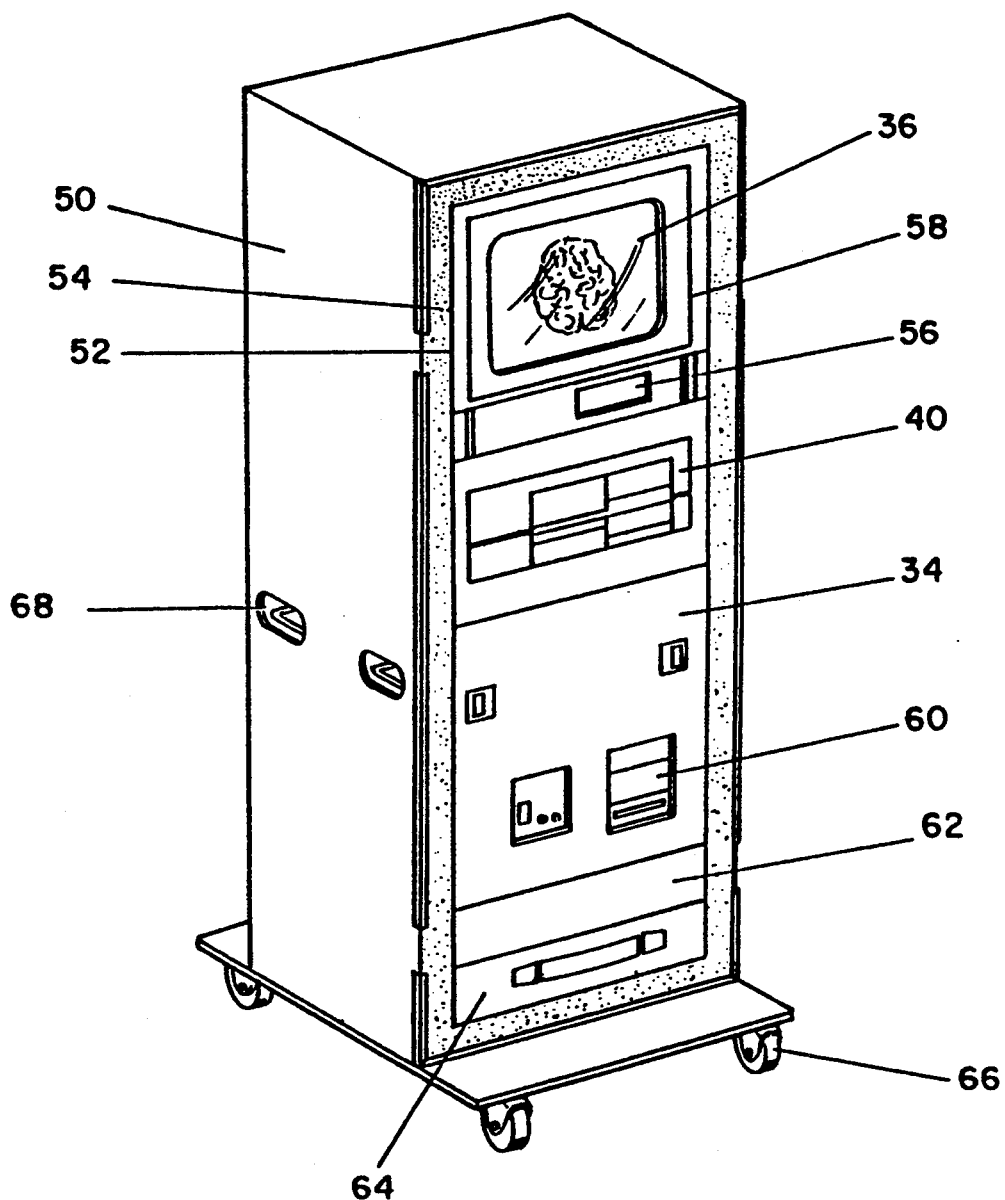
FIG. 3 is a perspective view of the preferred apparatus of the invention.

The preferred apparatus of the invention is illustrated in FIG. 3. The apparatus comprises an outer case 50 and an inner case 52 for housing the CPU 34, the monitor 36, the hard copy unit 40, and the computer video signal processor 62. A foam layer 54 for absorbing shock so that the apparatus can be easily transported is disposed between the outer case 50 and the inner case 52. Monitor controls 56 for adjusting, for instance, brightness, gain, and degauss, are provided. The monitor 36 preferably has disposed thereon a touch screen user interface 58 so that the surgeon or operator can provide input merely by touching the monitor screen with a stylus or finger. Storage modules 60 provide for storage of the image data. The computer video signal processor 62 converts the scanning data into a standard format for image enhancement and manipulation. A storage drawer 64 for storing tools, or the like, may be provided in the apparatus for ease of access by the operator. Handles 68, along with wheels or casters 66 on the bottom of the apparatus enable the apparatus to be easily moved, for instance from the scanning room to the operating room. Software usable with the apparatus hardware to practice and to carry out the desiderata of the invention is disclosed herewith.

The program listings in the microfiche appendix are directed to the programmed interface to computer video processor, an electrophysiological maps program, an anatomical maps program, a probe placement program, a stereotactic frame calibration program, an image overlay program, an icon layout program and a touchscreen control program. These programs are unique to the invention. Other programs used in practicing the invention, such as image manipulation programs, are either commercially available or within the skill of practitioners in the programming arts.

Although a brain anatomical map system was present in a rudimentary form, as published in the paper of Hardy, Koch, Lassiter (1983), it has subsequently been extensively improved for use with the invention.

In practicing the invention, a surgeon can acquire images by a direct coaxial link to various scanners and thereby avoid the cumbersome use of magnetic transport media.

At least two images should be obtained when the apparatus and method of the invention are used, one image at the level of the intended analysis and another image at the level of the entry point obtaining additional images enhances the accuracy and efficacy. These additional images are necessary for volumetric determinations. Volumetric determinations are helpful, for example, if the tumor is to be treated using implantation of radioactive isotopes. Preferably the images are stored and not lost when the apparatus is turned off, so that the apparatus can be easily transported from, for example, the scanner suite to the operating suite. This can be accomplished, in accordance with the invention, by storing the images on a hard disk.

For thalamotomies, it is useful to obtain images in approximately 1.5 mm increments in an area of between approximately 20 to 30 mm above the posterior clinoid process to include both the anterior and posterior commissures. Once images are acquired through the commissures, the thickness of the image sections can be increased both above and below the thalamic zone. This method reduces scanning time and decreases the radiation dose (when CT scanning is utilized) to the patient. The apparatus and method of the invention can be used to obtain a horizontal reformatted image along the intercommissure plane showing both the anterior and posterior commissures in the same image section. Most stereotactic surgeons regard the nucleus ventralis intermedius (V.i.m.) of the thalamus as the anatomical target site of choice for lesions in the treatment of dyskinesias. Other stereotactic surgeons prefer to extend the lesion slightly inferiorly into the dorsal subthalamic H-fields of Forel. The general target is small, and measures approximately 6 mm×4 mm×4 mm. The more inferior a lesion is made, the smaller it has to be to treat dyskinetic movements. Conversely, the higher a thalamic lesion is made, the larger it has to be to get equal results. The target area is bounded by important anatomical functional zones; that is, the motor fibers in the internal capsule laterally, the sensory nucleus posteriorly, the mammillothalamic bundle anteriormedially, and the subthalamic nucleus inferiorly. The invention allows for accurate lesion localization.

Fiducial markings should be present on all images so that calibration and probe positioning determinations can be achieved. Preferably, the surgeon can select the individual images to be calibrated. Frame calibration techniques, such as tacking fiducial marks on the images, are particularly useful in accordance with the invention.

Various electrodes or probes, common to the art, are useful in accordance with the invention. Two methods are useful in the preferred embodiment for defining the trajectory of the probe. In the first method, the entry point of the probe is designated by tacking it on the image. A target point on another scanner image slice is selected and the coordinates of the two points can then be used to determine a probe's spatial trajectory. In the second method, the trajectory of the probe can be defined by entering the probe's angles according to the stereotactic frame design, such as the anterior-posterior and lateral angles using a Leksell frame, or the angles of azimuth and declination (alpha, beta, delta, and gamma angles) using a Brown-Roberts-Wells (a registered trademark) frame. A target point on one image slice is chosen. Then the angles of the probe's spatial intersection with that point are entered. This defines the probe's spatial trajectory. The image acquisition and storage preferably takes approximately 15 minutes for approximately 20 images.

The invention is further illustrated by the following non-limiting example.

EXAMPLE

A preferred apparatus in accordance with the present invention is seen in FIG. 3. The invention consists of a container 58" high, 25½" wide, 31½" deep, with movable casters preferably having caster locks. This case is the main external package for the apparatus. It consists of an outer synthetic plastic cover with edges reinforced and bonded with. aluminum molding. The case is configured so that the front and back panels can be removed for exposure of the apparatus components. When the front and back panels are in place, the system can be locked to prevent unwanted access to the apparatus. The apparatus components are suspended in the outer case by an inner case of 52½" high, 19" wide 25" deep standard IEEE 19" rackmount frame around which is a 3" layer of shock absorbing foam. This configuration allows for easy transport of the apparatus with protection from shock. This case is airline approved and therefore can also act as a shipping container for the apparatus. Individual apparatus components can be fitted into the rackmount inner case. Such cases can be custom made from commercial manufacturers.

The invention also contains a 19" rackmount, high resolution (800×1024 or greater) color graphics monitor with standard video inputs for red, green, blue, and composite video. This particular monitor can be configured to operate in either an interlaced or non-interlaced mode at 60 Hz. It can also function to receive an RS-170 video standard or RS-343 video standard. Video display can be set at a 1:1 or 3:4 aspect ratio. The monitor CRT (cathode ray tube) screen is of the short persistence phosphorus type which is preferably for some of the system's functions (for example, flicker-frame and transparent overlays of scanned images). Monitor controls for brightness, gain, and degauss are readily available on the front panel of the monitor. These functions are preferable and it is important that they are readily available to the user. The brightness and gain can be used to vary the apparent intensity of an image appearing on the screen such that it can be easily viewed in various ambient light environments. In addition, the degauss feature is important since the system can be used in various magnetic environments without distortion of the image. The monitor's image is driven by a frame grabber image acquisition and image output board housed in the system's computer. The monitor's RGB and composite video inputs can be looped through the monitor so that video hard copy images can be taken directly from the monitor's output. The monitor also has capabilities of either a high resistance or 75 ohms termination. Such monitors are standard and commercially available.

The infrared touchscreen system consists of a commercially available infrared touchscreen which is custom configured to mount under an infrared transparent bezel around the perimeter of the 19" monitor so that the full extent of the CRT screen is available for use. The infrared touchscreen consists of an inner bezel which contains an array of infrared diodes and detectors which project an invisible to the eye infrared beam matrix over the front of the CRT screen. This touchscreen is designed so that whenever an instrument (stylus or finger) is placed in the infrared matrix such interruption is detected and its spatial coordinates are transmitted to the computer system via a standard RS-232 (IEEE standard) serial input/output communications interface. Special software drivers control the operation of the touchscreen, although software drivers can also be obtained commercially. The touchscreen interface allows the surgeon to interface with the system during an operative procedure in a sterile fashion by either the use of a sterile stylus or a sterile gloved finger. The user does not have to "touch" anything in order to activate the system since this is done by interrupting the touchscreen's infrared beams. In addition, the user avoids the cumbersome and confusing use of keyboards, joysticks, mouse or other such input control devices in the use of the system. Control through the touchscreen is by pointing at icons (picturegrams) which are present as a menu system on the monitor CRT display. Pointing at such an icon interrupts the coordinate locations for that icon which is transmitted to the system's computer which then carries out certain functions inherent in the commands which can be executed by that icon.

Figure 4:
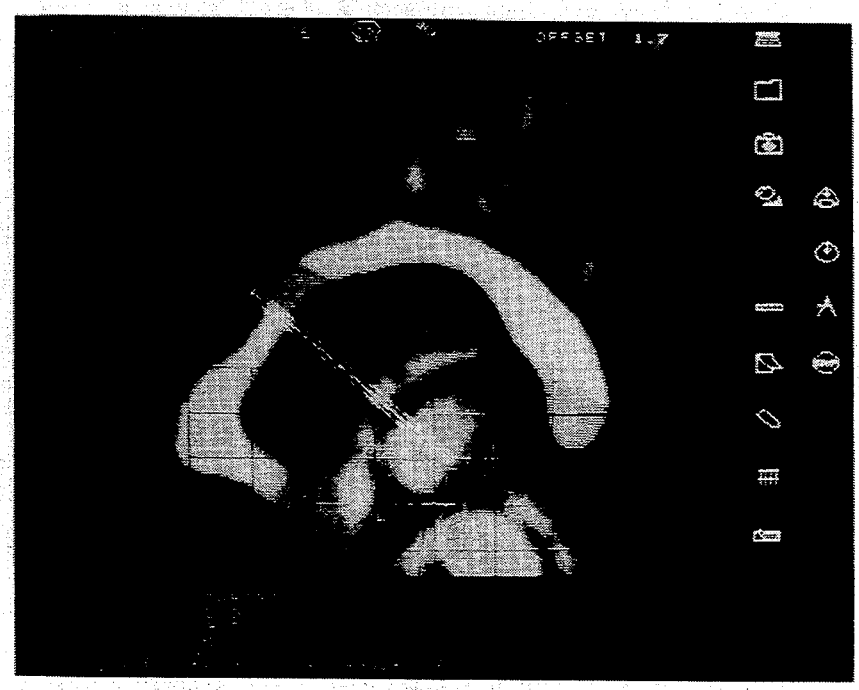
FIGS. 4–12 show various brain images depictable on the monitor of the FIG. 3 apparatus.
Figure 5:
Figure 6:
Figure 7:
Figure 8:
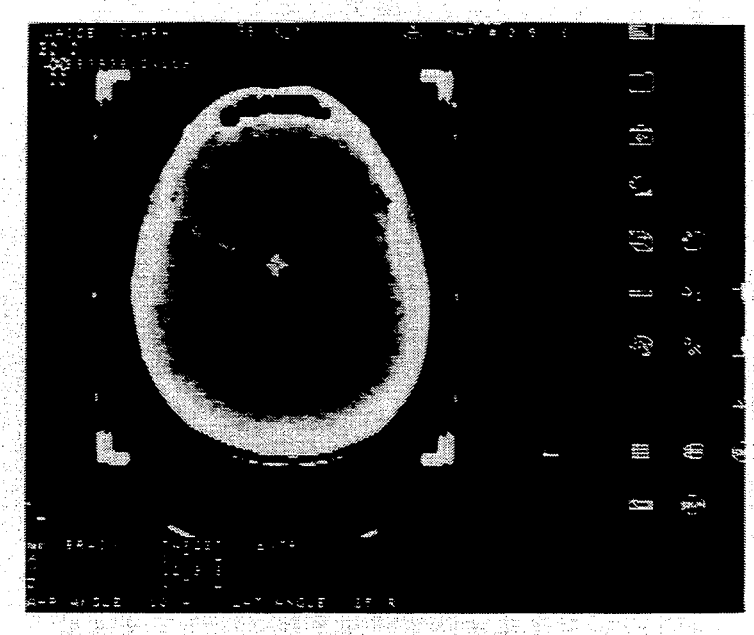
Figure 9:
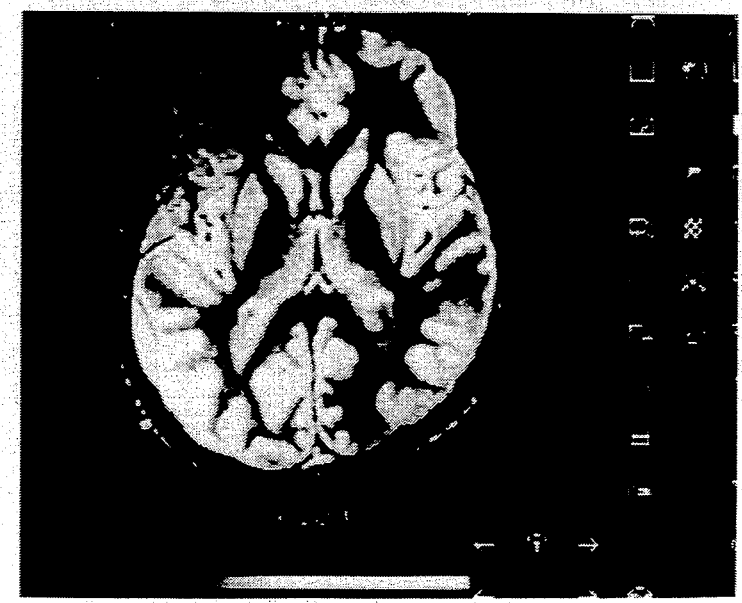
Figure 10:
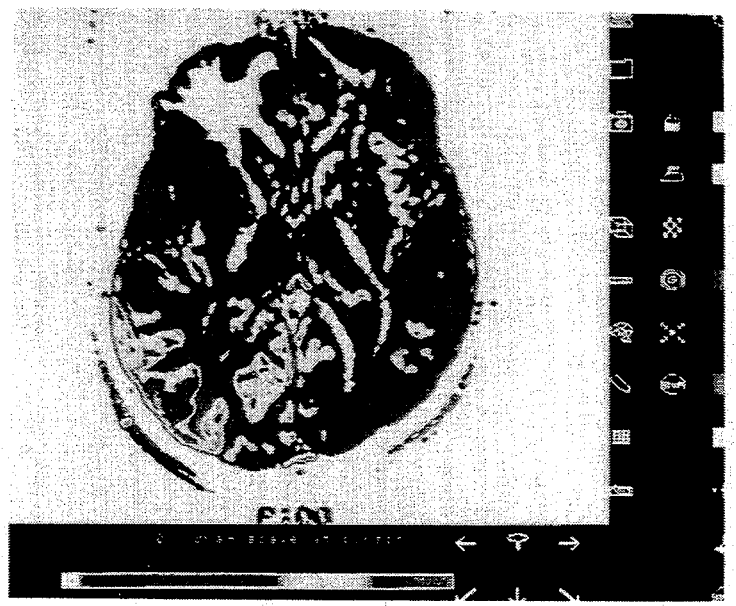
Figure 11:
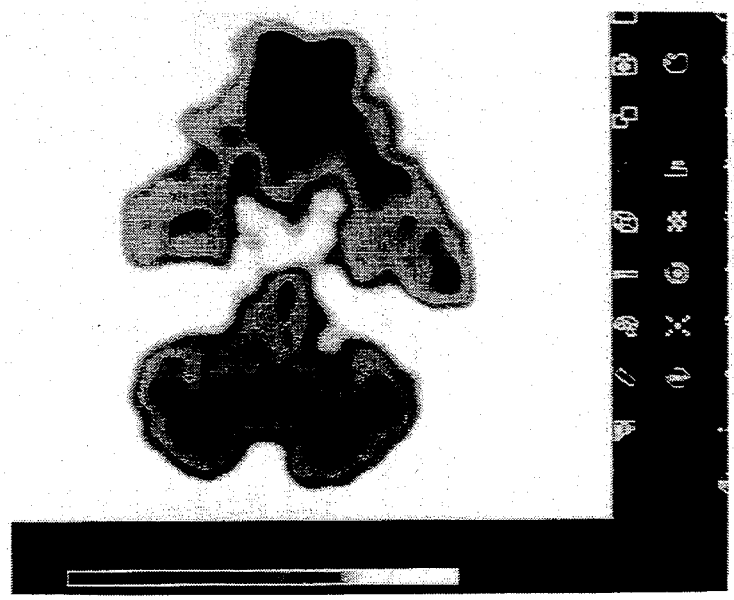
Figure 12:
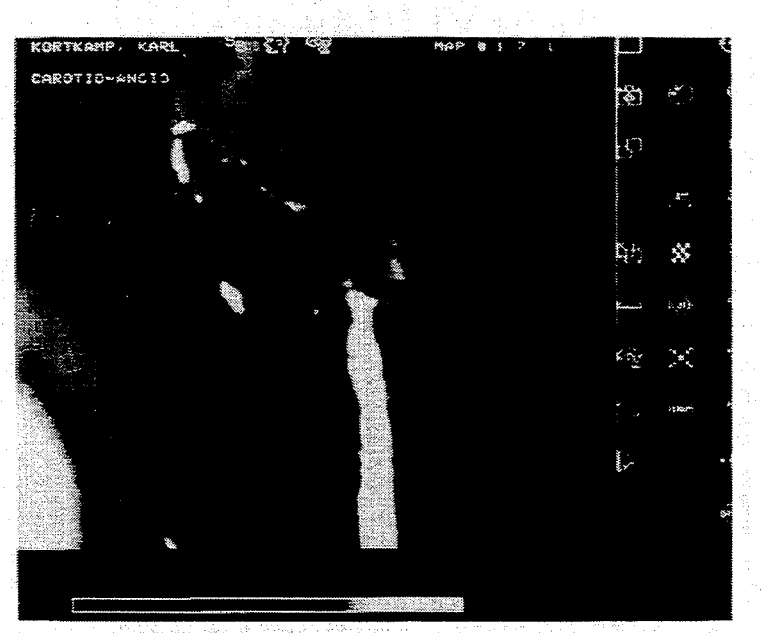

The color video thermal hard copy unit is commercially available and is capable of accurately reproducing any image displayed on the 19" color graphics monitor. Input to the system is from the loop-through of the RGB outputs from the color graphics monitor. This unit has its own frame memory such that by activation of its memory function, it can save within its memory, in digital format, an image displayed on the CRT screen. An image thus obtained can then be printed on various hard copy media for storage. Examplary hard copy video prints of images obtainable using the invention are illustrated in FIGS. 4 12. FIG. 4–12 are color images of the brain obtained by the apparatus of the invention through a computer display. FIG. 4 is a saggital NMR image with brain map overlay and simulated probe positioning for target. FIG. 5 is a magnified display showing brain maps and electrophysiological maps. FIG. 6 is an image from a computer display showing a CT image with fudicial markings about the periphery. FIG. 7 is an image similar to FIG. 6, which shows deep seated brain tumor with simulated probe trajectory noted. FIG. 8 is a CT image with the Leksell stereotactic frame and associated fudicial markings, where no probe simulation is shown. FIG. 9 is an NMR image of the brain. FIG. 10 is another NMR image of the brain. FIG. 11 is a PET image of the brain. FIG. 12 is a DSA image of the brain. The target coordinates of FIGS. 4–12 are shown for each on the image of the computer display.

The unit's color selection range, intensity, brightness, and contrast can be controlled by the user through the use of selected control knobs housed in the front of the unit. This unit is used to make selected hard copy archives of images displayed on the CRT screen. An additional advantage of this particular unit is that it is small, compact, easily serviced and used by the end user. Paper and film can be easily placed in the system by the use of cartridge loaders and is therefore easy to prepare by the user.

The CPU comprises the various hardware components and software components for the central functioning of the apparatus. All hardware components are commercially available and have been integrated in such a fashion to achieve the desired features and functions of the invention. Various components of the computer processing unit are as follows:

Component 1: Central Processing Unit (CPU). The central processing unit consists of a VME bus based computer as is commonly manufactured by Motorola Corporation and other corporations in the United States and is a European Common Market standard where it is called the EuroCard. The present system runs on a 68020 processor at 16.67 mHz. The system has 8 megabytes of dynamic random access memory (DRAM). This particular system configuration, that is, the VME bus, was selected for ease of design, future upgrades and service. It must be noted that the software routines of the invention can be used on other computers; for example, IBM registered trademark PC, AT, XT, or P2, or such similar systems, the DEC VAX registered trademark, SUN VME systems or other such similar systems. The software can also run on considerably faster CPUs. The central processing unit is configured such that the system automatically boots itself up upon power-on. It has at least one RS-232 port through which communication is directed to and from the infrared touchscreen.

Component 2: Archiving and Storage Modules. The archiving and storage modules consist of a 5¼"1 mb floppy disk drive; at least an 86 mb Winchester hard disk drive; and at least a 60 mb streaming tape cartridge tape drive. These components are used to house the system's software operating system and programs (Winchester hard disk) and to save patient and image data. The system's operating system is a standard UNIX base software system which is either an AT&T or Berkeley UNIX standard which is commercially available.

Component 3: Image Acquisition Interface. The image acquisition interface consists of several components which are:

a) VME bus base framegrabber video display board with a minimal configuration of 12/16 bit graphics overlay display capability. This component is commercially available and is capable of converting a standard (RS-170) or non-standard video signal to a digital format which is stored in its memory. Such images are stored as an 8 bit deep image with gray scales of 256 levels. Such stored images can then be displayed through either a red, green, blue (RGB) video output or a composite video output in either interlaced or non-interlaced mode to the high resolution color graphics monitor. The board has at least four to eight additional bit planes available for graphics overlay. This configuration allows the simultaneous display of multiple images (combination of scanned images or graphic images) on the same monitor for composite viewing. In addition, such images can be independently manipulated as subsets without interference to other images. This configuration allows the very rapid and non-destructive manipulation of multiple images in a common display. Image output is as a standard RS-170 video format. This board will accept inputs from a standard videoscan converter, camera interface, or video tape input or directly from the system's CPU.

b) VME bus based Ethernet board. This board is a commercially available communications data acquisition board which can transfer digitized non-standard video input data in a standard format (ARC-NEMA) from a common communication network between various scanning devices and store them as digital data in memory. Images acquired in this fashion and stored in the computer system's memory can then be transferred to the memory of the framegrabber video display board as noted in a) above. Images from non-standard video can be digitized in this fashion for eventual display in a standard format; for example, CT scans, NMR scans, PET scans, isotope scans, and others. Video inputs through this board do not allow real time viewing but are capable of giving a slightly clearer image. In addition, this configuration allows the invention to acquire and utilize images from a common network which may be present in some hospital settings. This represents an alternative source from image acquisition and conversion from a common format as noted in c) below.

c) Computer video processor (CVP). This component is commercially available and is capable, apart from the Ethernet board noted above, of converting all non-standard video signals into a common RS-170 video format. This component is configured by the programming of a special chip in its own separate central processor to acquire a wide variety of non-standard video signals within a certain designated range. As used in the invention, the range is set so that it can convert signals for CT scans, NMR scans, PET scans, DSA, etc., into a common format. The parameters which can be set preferably include at least all of the following signal parameters:

1. horizontal front porch
2. horizontal back porch
3. vertical front porch
4. vertical back porch
5. horizontal blanking time 6. vertical blanking time
7. pixel clock rate
8. horizontal frequency
9. vertical frequency
10. horizontal sync width
11. vertical sync width
12. vertical refresh rate
13. composite video voltage level
14. non-composite video voltage level
15. line rate The input to this unit is via a standard 75 ohm BNC connector from various scanner imaging sources. Such scanning imaging sources are then processed by the central processor unit portion of the computer video processor and converted to RS-170 standard signal output. The signal output as RS-170 format is inputted into the framegrabber video display board for further processing and output. Images inputs through this part of the system allow continuous real time viewing. The clarity of some images may be slightly reduced due to signal averaging. The CVP has external switching capabilities which can set the specific parameters as noted in the above list. As commercially available these external switches are 16 in number and consist of:

1. Preset field blanking #1
2. Preset field blanking #2
3. Preset input divider #1
4. Preset input divider #2
5. 32 kHz (nomial mode)
6. Custom preset parameters (special EPROM chip interface.
7. Tester mode
8. Freeze frame
9. Swap fields 1 and 2
10. Decrement field blanking
11. Narrow input clock
12. Widen input clock
13. Move image left
14. Move image right
15. Narrow output clock
16. Widen output clock A programmable switching interface which consists of a VME bus based digital relay board with 16–32 independent switches can be programmed for activation through the computer. The interface between the relay board and the switch input is via a specially wired input/output box between these two levels of communication. Alternatively, a scanner converter automatically senses signal input and sets parameters for conversion to a standard format, without the use of user selectable switches.

Data entering into the system is from various scanning modalities via a standard 75 ohm video cable with standard BNC connectors. This cable carries a composite video output from any of the respective scanning devices and enters directly into the VME bus based framegrabber video display board (imaging board) if it is an RS-170 (CCIR or NTSC) video standard, for example, a standard RS-170 video camera input, recording device or some scanners which output an RS-170 standard. If the output from the scanner is a non-standard video output, e.g., CT scan, NMR scan, PET scan, DSA scan, and others, then the input is into the computer video processor unit. At the level of the computer video processor unit, the non-standard video signal is analyzed and converted by the system's signal processor and converted to a standard RS-170 video output which then is output to the VME bus based framegrabber display board. In addition, at the level of the computer video processor specific switchable parameters for analysis and conversion of the incoming non-standard composite video scanner output are set via a relay control board which is selectable through a programmed interface in the apparatus computer. Software in the system allows such parameters to be set so that the user can indicate which scanner images are being acquired. In some cases the RS-170 video standard output or other non-standard video outputs, e.g., RS-343, RS-344, from various scanning devices can either be in the form of a composite video output signal or as a TTL format with separate horizontal and vertical sync outputs and a pixel clock pulsed output. The system is capable of acquiring images in either manner.

An alternate source of image acquisition may be obtained from a common Ethernet communications network between various scanners. Data from this communications network may be available as a common standard, ARC-NEMA, which the system through its Ethernet board may acquire images for its use. In such cases, the computer video processor would be bypassed and images acquired through the Ethernet board communications network is interfaced directly with the video display board.

At the level of the VME bus based framegrabber video display board the RS-170 video standard input (or input via the Ethernet) is digitized in frame memory in an $512 \times 512 \times 8$-bits deep format. With this configuration images can be stored with up to 256 gray scale pixel levels. Images digitized into the framegrabber board can then either be stored in the system's dynamic memory or in the system's memory storage units (Winchester disk, floppy disk, or streaming tape). Images stored in such fashion are archived by the software system and can be recalled for rapid display on a 19-inch high resolution color graphics video display monitor. The output to the monitor is via a standard RGB color video output with the sync pulse on the green output.

The CPU controls all data inflow and outflow through its special software programs. The image display board has 4 to 8 bits of image overlay capability which the system utilizes through its software routines to make composite images, for example, graphic overlays, brain maps, probe, electro-physiological maps, measurements, alpha-numeric data and various calculated parameters. One set of software routines listings, used in accordance with the invention, are appended hereto in the microfiche appendix and are hereby incorporated by reference into the specification. These routines include the following: Programmed interfaces to computer video processor; electro-physiological maps program; anatomical map program; probe placement program; stereotactic frame calibration program; image overlay program; icon layout program; and touchscreen control program. The image manipulation programs are commercially available.

The CPU's functions are directed by the user through the use of an infra-red touchscreen which has an input via a standard RS-232 8-bit input-output serial interface into the CPU. The user directs the functions of the unit by pointing at various icons (picturegrams) which are displayed on the monitor's cathode ray tube. The act of pointing at an icon displayed on the CRT screen within the confines of the infra-red touchscreen matrix directs the CPU to institute a predetermined series of programmed functions specific to the user's desires and within the parameters of the then existing software design.

Through a standard loop-through off of the high resolution color graphics monitor, a standard video thermal hard copy unit is attached for the production of hard copy archives. The user can activate this unit by selecting certain switchable parameters on the front of the unit.

The invention has been described in detail with particular reference to a preferred embodiment thereof, but it will be understood that variations and modifications can be effected within the scope of the invention.

I claim:

1. An apparatus for generating a presentation of images from a variety of imaging sources, the apparatus comprising:
   means for acquiring a plurality of images from a plurality of separate imaging sources;
   means for converting said plurality of images into a selected format;
   means for storing said plurality of images;
   means for selectively recalling and displaying at least two images of said plurality of images upon a single display device;
   means for manipulating at least one of said at least two images independently of the other image;
   means for comparing said at least two images;
   means for determining stereotactic coordinates and performing volumetric determinations from said at least two images; and
   means for determining distances and areas from said at least two images.

2. The apparatus of claim 1 wherein said means for acquiring a plurality of images comprises means for acquiring body part-related images with at least one of said images being of an actual patient's body part.

3. The apparatus of claim 2 wherein said means for acquiring body part-related images comprises means for acquiring brain-related images with at least one of said images being of the actual patient's brain.

4. The apparatus of claim 3 wherein said means for acquiring said brain-related image further comprises means for obtaining at least one image from a brain map atlas.

5. The apparatus of claim 4 wherein said brain map atlas comprises a composite of brain maps.

6. The apparatus of claim 4 wherein said means for manipulating at least one of said at least two images comprises means for manipulating said image from the brain map atlas to conform to said image of the patient's brain.

7. The apparatus of claim 3 further comprising means for displaying a representation of the patient's brain selected from the group consisting of anatomical configurations, physiological configurations, electrophysiological configurations, and combinations thereof.

8. The apparatus of claim 3 wherein said means for determining distances and areas comprises means for obtaining within the actual patient's brain, the distance between two points within the patient's brain and the area of a selected portion of the patient's brain.

9. The apparatus of claim 3 wherein said means for determining distances and areas comprises means for obtaining within the actual patient's brain, the volume of a selected part of the patient's brain.

10. The invention of claim 9 further comprising means for simulating a surgical device and determining trajectory of said device comprising:
    means for locating the target point on an image of the patient's brain;
    means for intersecting said target point by deriving the anterior-posterior and lateral angles of the device, wherein said angles are derived by using a stereotactic device.

11. The apparatus of claim 10 wherein said means for intersecting said target point comprises means for deriving azimuth and declination angles of said stereotactic device.

12. The apparatus of claim 11 wherein said azimuth and declination angles are derived using said stereotactic device.

13. The apparatus of claim 3 wherein said means for manipulating said images further comprises means for manipulating and swapping brain anatomical images in frontal, sagittal and horizontal sections.

14. The apparatus of claim 1 wherein said image acquiring means comprises means for obtaining at least one said image directly from at least one imaging source without the use of magnetic transport media.

15. The apparatus of claim 1 wherein said image acquiring means comprising media means for obtaining at least one said image by the use of magnetic transport.

16. The apparatus of claim 1 wherein said image acquiring means comprises a direct coaxial link with at least one imaging source.

17. The apparatus of claim 1 wherein at least one imaging source comprises a scanner source selected from the group consisting of computerized axial tomography (CT) scanners, nuclear magnetic resonance (NMR) scanners, positron emission tomography (PET) scanners, isotope scanners, digital substraction angiography (DSA) scanners, and X-ray scanners.

18. The apparatus of claim 1 wherein at least one imaging source comprises a video source.

19. The apparatus of claim 1 wherein said recalling and displaying means comprises means for selectively recalling and displaying an image comprising references for stereotactic localization.

20. The apparatus of claim 1 further comprising user means to input data within a sterile environment.

21. The apparatus of claim 1 wherein said means for acquiring a plurality of images comprises means for acquiring a predetermined number of image types.

22. The apparatus of claim 21 wherein said means for acquiring a predetermined number of image types comprises means for acquiring different image types from a single imaging source.

23. The apparatus of claim 1 further comprising means for manipulating both of said at least two images independently of each other.

24. The apparatus of claim 1 wherein said means for manipulating at least one of said at least two images comprises means for shaping and sizing at least one of said at least two images.

25. The apparatus of claim 24 wherein said means for manipulating comprises means for shaping and sizing at least one of said images to conform to at least one other said image in shape and size.

26. The apparatus of claim 1 further comprising means for superimposing at least one of said at least two images upon the other of said at least two images.

27. The apparatus of claim 1 wherein said manipulating means comprises at least one means selected from the group consisting of filtering, smoothing, sharpening, pseudocoloring, and edge detection means.

28. The apparatus of claim 27 wherein said edge detection means comprises means for executing at least one routine selected from the group consisting of Laplacian, Roberts, Sorbel, and Frei routines.

29. The apparatus of claim 1 further comprising means for recording and archiving the procedural use of said apparatus.

30. The apparatus of claim 1 further comprising means for providing stereotactic coordinates for a user selected point on the presentation.

31. The apparatus of claim 1 further comprising means for simulating at least one image.

32. The apparatus of claim 31 wherein said simulating means comprises means for simulating at least one acquired image.

33. The apparatus of claim 31 wherein said means for simulating is selected from the group consisting of simulating at least one two-dimensional graphic image, and simulating at least one three-dimensional graphic image.

34. The apparatus of claim 31 wherein said simulated image comprises a composite of images.

35. The apparatus of claim 34 wherein said simulated image comprises a composite of manipulated images.

36. The apparatus of claim 35 wherein said simulating means comprises means for independently manipulating components of said composite of images as subsets.

37. The apparatus of claim 36 wherein said simulating means comprises means for manipulating said subsets independently of other said images.

38. The apparatus of claim 1 wherein said displayed images comprise a composite of images.

39. The apparatus of claim 38 wherein said composite of images comprises at least one said acquired image and one simulated image.

40. The apparatus of claim 39 wherein said recalling and displaying means comprises means for independently manipulating said acquired image and said simulated image.

41. The apparatus of claim 1 further comprising an infrared grid disposed across said image displaying device.

42. The apparatus of claim 1 further comprising means for simulating at least one device selected from the group consisting of stereotactic devices, probes, electrodes, implantation devices, and needles.

43. The apparatus of claim 42 further comprising means for simulating manipulation of said device.

44. The apparatus of claim 42 wherein said device comprises an isodose implantation device and said apparatus further comprises means for determining optimum placement for isodose implantation, means for determining optimum dosage for isodose implantation, and means for simulating an isodose implant.

45. The apparatus of claim 1 wherein said means for determining stereotactic coordinates further comprises means for determining stereotactic coordinates of at least one entry point, target point, placement point and trajectory of a device.

46. The apparatus of claim 1 further comprising means for pixel analysis.

47. The apparatus of claim 46 wherein said means for pixel analysis comprises means for pixel analysis of an image selected from the group consisting of an entire image, a user-defined area of an image and a combination thereof.

48. The apparatus of claim 47 further comprising means for selecting image data on said images on the basis of said pixel analysis.

49. The apparatus of claim 48 further comprising means for generating composite images from said image data so as to provide at least one representation selected from the group consisting of anatomical configurations, physiological configurations, electrophysiological configurations, and combinations thereof, of a patient's brain.

50. The apparatus of claim 1 wherein said means for recalling and displaying comprises video presentation means.

51. The apparatus of claim 1 wherein said means for recalling and displaying comprises means for displaying images independent of the imaging sources.

52. The apparatus of claim 1 further comprising means for coding and storing representations of physiological response points and means for selectively recalling and displaying any of said response points within the presentation.

53. A method for generating a presentation of images from a variety of imaging sources, the method comprising the steps of:
acquiring a plurality of images from a plurality of separate imaging sources;
converting the plurality of images into a selected format;
storing the plurality of images;
selectively recalling and displaying at least two images of the plurality of images upon a single display device;
manipulating at least one of the at least two images independently of the other image;
comparing the at least two images;
determining stereotactic coordinates and performing volumetric determinations from the at least two images; and determining distances and areas from the at least two images.

54. The method of claim 53 wherein the step of acquiring a plurality of images comprises acquiring body part-related images with at least one image being of the actual patient's body part.

55. The method of claim 54 wherein the step of acquiring body part-related images comprises acquiring brain-related images with at least one of the images being of the actual patient's brain.

56. The invention of claim 55 wherein the step of acquiring the brain-related image further comprises obtaining at least one image from a brain map atlas.

57. The method of claim 56 wherein the step of obtaining at least one image from a brain map atlas comprises the step of obtaining at least one image from a composite of brain maps.

58. The method of claim 56 wherein the step of manipulating at least one of the at least two images comprises manipulating the image from the brain map atlas to conform to the image of the patient's brain.

59. The method of claim 55 further comprising displaying a representation of the patient's brain selected from the group consisting of anatomical configurations, physiological configurations, electrophysiological configurations, and combinations thereof.

60. The method of claim 55 wherein the step of determining distances and areas comprises obtaining within the actual patient's brain, the distance between two points within the patient's brain and the area of a selected portion of the patient's brain.

61. The method of claim 55 wherein the step of determining distances and areas comprises obtaining within the actual patient's brain, the volume of a selected part of the patient's brain.

62. The method of claim 61 further comprising simulating a surgical device and determining trajectory of the device comprising:
locating the target point on an image of the patient's brain; and
intersecting the target point by deriving the anterior-posterior and lateral angles of the device, wherein the angles are derived using a stereotactic device.

63. The method of claim 62 wherein intersecting the target point comprises deriving azimuth and declination angles of said stereotactic device.

64. The method of claim 63 wherein the azimuth and declination angles are derived using said stereotactic device.

65. The method of claim 55 wherein the step of manipulating the images further comprises manipulating and swapping brain anatomical images in frontal, sagittal and horizontal sections.

66. The method of claim 55 further comprising actually executing functional and morphological stereotactical procedures for brain targets selected from the group consisting of dyskinesias, pain syndromes, tumors, lesions, aneurysms, seizure disorders, functional anatomical sites, physiological response points, blood vessels, abnormalities and neuropathological conditions.

67. The method of claim 52 wherein the step of acquiring images comprises obtaining at least one of the images directly from at least one imaging source without the use of magnetic transport media.

68. The method of claim 52 wherein the step of acquiring images comprises obtaining at least one of the images by the use of magnetic transport media.

69. The method of claim 52 wherein the step of acquiring images comprises providing a direct coaxial link with at least one imaging source.

70. The method of claim 53 wherein the step of acquiring images comprises the step of acquiring images from at least one imaging source comprising a scanner source selected from the group consisting of computerized axial tomography (CT) scanners, nuclear magnetic resonance (NMR) scanners, positron emission tomography (PET) scanners, isotope scanners, digital substraction angiography (DSA) scanners, and X-ray scanners.

71. The method of claim 53 wherein the step of acquiring images from at least one imaging source comprises the step of acquiring images from a video source.

72. The method of claim 53 wherein the step of acquiring images further comprises the step of providing references for stereotactic localization.

73. The method of claim 53 further comprising the step of providing for a user to input data within a sterile environment.

74. The method of claim 53 wherein the step of acquiring the plurality of images comprises the step of acquiring any of a predetermined number of image types.

75. The method of claim 74 wherein the step of acquiring the plurality of images from the separate image sources comprises the step of acquiring different types of images from a single type of imaging source.

76. The method of claim 53 further comprising manipulating both of the images independently of each other.

77. The method of claim 53 wherein the step of manipulating the at least two images comprises shaping and sizing at least one of the at least two images.

78. The method of claim 77 wherein the step of manipulating comprises shaping and sizing at least one of the images to conform to at least one other image in shape and size.

79. The method of claim 53 further comprising superimposing at least one of the at least two images upon the other of the at least two images.

80. The method of claim 53 wherein the step of manipulating the at least two images comprises utilizing at least one procedure selected from the group consisting of filtering, smoothing, sharpening, pseudocoloring, and edge detection.

81. The method of claim 80 wherein the edge detection procedure comprises at least one routine selected from the group consisting of Laplacian, Roberts, Sorbel, and Frei routines.

82. The method of claim 53 further comprising recording and archiving the method.

83. The method of claim 53 further comprising providing stereotactic coordinates for a user selected point on the presentation.

84. The method of claim 53 further comprising the step of simulating at least one image.

85. The method of claim 84 wherein the step of simulating at least one image comprises the step of simulating at least one acquired image.

86. The method of claim 84 wherein the step comprising simulating at least one image is selected from the group consisting of simulating at least one two-dimensional graphic image and simulating at least one three-dimensional graphic image.

87. The method of claim 84 wherein the step of simulating at least one image comprises the step of simulating a composite of images from more than one imaging source.

88. The method of claim 87 wherein the step of simulating at least one image comprises the step of simulating a composite of manipulated images.

89. The method of claim 88 further comprising the step of independently manipulating components of the composite image as subsets.

90. The method of claim 89 further comprising the step of independently manipulating the subsets independently of the other images.

91. The method of claim 53 wherein the displaying of images comprises displaying a composite of images.

92. The method of claim 91 wherein the step of displaying a composite of images comprises the step of displaying at least one acquired image and one simulated image.

93. The method of claim 92 further comprising the step of independently manipulating the acquired image and the simulated image.

94. The method of claim 53 further comprising the step of utilizing an infrared grid disposed across the image displaying device.

95. The method of claim 53 further comprising simulating at least one device selected from the group consisting of stereotactic devices, probes, electrodes, implantation devices, and needles.

96. The method of claim 95 further comprising simulating manipulation of the device.

97. The method of claim 95 wherein the device comprises an isodose implantation device and the method further comprises determining optimum placement for isodose implantation, determining optimum dosage for isodose implantation and simulating an isodose implant.

98. The method of claim 53 wherein the step of determining stereotactic coordinates further comprises determining stereotactic coordinates of at least one entry point, target point, placement point and trajectory of a device.

99. The method of claim 53 further comprising providing pixel analysis.

100. The method of claim 99 wherein the step of providing pixel analysis is selected from the group consisting of providing pixel analysis to an entire image, a user-defined area of an image and a combination thereof.

101. The method of claim 100 further comprising means for selecting image data on the images on the basis of the pixel analysis.

102. The method of claim 101 further comprising the step of generating composite images from the image data so as to provide at least one representation selected from the group consisting of anatomical configurations, physiological configurations, electrophysiological configurations, and combinations thereof, of a patient's brain.

103. The method of claim 53 wherein step of generating a presentation of the images comprises the step of generating a video presentation.

104. The method of claim 53 wherein the step of generating a presentation of images is independent of the step of acquiring a plurality of images from a plurality of separate imaging sources.

105. The method of claim 53 further comprising coding and storing representations of physiological response points and selectively recalling and displaying any of the response points within the presentation.

106. The method of claim 53 further comprising the steps of:
  a) providing an image acquiring apparatus;
  b) providing a stereotactic reference system to a patient;
  c) placing the patient's body part to be analyzed in the imaging source;
  d) acquiring the images desired using the image source;
  e) saving and storing the acquired image in the apparatus;
  f) taking the apparatus and the patient into the operating suite;
  g) using image manipulation routines in the apparatus to calibrate the desired image areas;
  h) using image manipulation routines in the apparatus to enhance desired image areas; and
  i) using the apparatus to determine desired coordinates.

107. The method of claim 106 further comprising using a brain map to precisely define the desired coordinates.

108. The method of claim 106 further comprising determining volumetric regions of the brain.

109. The method of claim 106 further comprising simulating brain surgical procedures.

* * * * *